United States Patent [19]

Penner et al.

[11] Patent Number: 4,830,952
[45] Date of Patent: May 16, 1989

[54] LANGMUIR-BLODGETT FILM ASSEMBLY

[75] Inventors: Thomas L. Penner, Fairport; John M. Noonan, Rochester; Ignazio S. Ponticello, Pittsford, all of N.Y.

[73] Assignee: Eastman Kodak Company, Rochester, N.Y.

[21] Appl. No.: 118,103

[22] Filed: Nov. 6, 1987

[51] Int. Cl.$^4$ .................. G03C 1/68; G03C 1/78; G03C 1/00
[52] U.S. Cl. .................. 430/287; 430/270; 430/281; 430/286; 430/495; 430/496; 430/935
[58] Field of Search ............... 430/270, 281, 288, 287, 430/935

[56] References Cited

U.S. PATENT DOCUMENTS

| | | | |
|---|---|---|---|
| 3,879,204 | 4/1975 | Gervay | 430/259 |
| 4,348,329 | 9/1982 | Chapman | 522/171 |
| 4,439,514 | 3/1984 | Garito | 430/272 |
| 4,536,450 | 8/1985 | Garito | 428/411.1 |
| 4,581,315 | 4/1986 | Garito | 430/270 |
| 4,686,169 | 8/1987 | Yoshino et al. | 430/961 |

OTHER PUBLICATIONS

G. L. Gaines, "On the History of Langmuir–Blodgett Films", First International Conference on Langmuir–Blodgett Films, *Thin Solid Films*, vol. 99, pp. ix–xiii, 1983.

P. Stroeve, M. P. Sprinivasan, and B. G. Higgins, "Langmuir–Blodgett Multilayers of Polymer-Mer-cyanine-Dye Mixtures", *Thin Solid Films*, vol. 146, pp. 209–220.

B. Tieke, G. Lieser and G. Wegner, "Polymerization of Diacetylenes in Multilayers", *Journal of Polymer Science: Polymer Chemistry Edition*, vol. 17, pp. 1631–1644 (1979).

F. Nakanishi, S. Okada, and H. Nakanishi, "Photoreaction of Long-Chain Mono n-Alkyl Esters of p--Phenylenediacrylic Acid in Multilayer Films", *Polymer Communications*, vol. 27, Aug. 1986, pp. 238 and 239.

H. Koch, A. Laschewsky, H. Ringsdorf, and K. Teng, "Photodimerization and Photopolymerization of Amphiphilic Cinnamic Acid Derivatives in Oriented Monolayers, Vesicles and Solution", *Makromol. Chem.*, vol. 187, pp. 1843–1853 (1986).

E. Elbert, A. Laschewsky, and H. Ringsdorf, "Hydrophilic Spacer Groups in Polymerizable Lipids: Formation of Biomembrane Models from Bulk Polymerized Lipids", *J. Am. Chem. Soc.*, vol. 107, 1985, pp. 4134–4141.

*Primary Examiner*—Paul R. Michl
*Assistant Examiner*—C. D. RoDee
*Attorney, Agent, or Firm*—Carl O. Thomas

[57] ABSTRACT

An article is disclosed containing a Langmuir-Blodgett film assembly comprised of at least one oriented polymer layer of monomolecular thickness containing repeating units comprised of a hydrophilic group linking two hydrophobic groups each containing at least two crosslinking moieties.

17 Claims, No Drawings

LANGMUIR-BLODGETT FILM ASSEMBLY

FIELD OF THE INVENTION

The invention relates to coated articles. More specifically, the invention relates to articles containing molecularly oriented coated layers. In a specific application the invention relates to optical articles.

BACKGROUND OF THE INVENTION

G. L. Gaines, "On the History of Langmuir-Blodgett Films", First International Conference on Langmuir-Blodgett Films, *Thin Solid Films,* Vol. 99, pp. ix–xiii, 1983, provides a brief historical review of the early investigations of the monomolecular oriented films initially produced by the spreading of oils at a water-air interface and transferred to a support by dipping. Langmuir-Blodgett films (hereinafter also referred to as LB films) have been recently the subject of renewed investigations, since they offer an attractive approach for forming an assembly ranging from one to many superimposed layers, each layer being of monomolecular thickness and formed of molecules that are spatially aligned.

LB film assemblies are of particular interest in the fabrication of optical articles, including both those which have linear and nonlinear optical transmission properties. The preparation of an LB film assembly showing indications of nonlinear optical properties is reported by P. Stroeve, M. P. Sprinivasan, and B. G. Higgins, "Langmuir-Blodgett Multilayers of Polymer-Mercyanine-Dye Mixtures", *Thin Solid Films,* Vol. 146, pp. 209–220. LB films were formed of mixtures of merocyanine dyes and poly(methyl methacrylate).

Although LB films and film assemblies have drawn interest, there have remained some significant concerns. One of the concerns associated with LB film assemblies is the structural integrity and stability of the layers. Another concern relates to the areal definition of LB films. Since LB films are deposited by drawing a support through a liquid phase interface, initial deposition of the film often covers a greater area of the support than is wanted for a particular application. For example, in integrating an optical waveguide prepared as an LB film assembly with a semiconductor chip support containing an integrated circuit, it may be desirable to define precisely the areal interface of the semiconductor chip support and the waveguide.

Prior to the present invention attempts have been made to produce photopolymerized LB films. Garito U.S. Pat. No. 4,439,514 reports in Examples 24 and 25 the formation of LB films through the deposition of the diynes pentacosa-10,12-diynoic acid and N-d(+)(α-methylbenzyl)-10,12-pentacosadiynamide, respectively. While the UV and X-ray stimulated crosslinking of these monomers was reported to yield excellent pattern definition, radiation crosslinked diyne polymer films have suffered the disadvantage of physical imperfections (e.g., cracks and fissures). B. Tieke, G. Lieser and G. Wegner, "Polymerization of Diacetylenes in Multilayers", *Journal of Polymer Science: Polymer Chemistry Edition,* Vol. 17, pp. 1631–1644 (1979) is considered a cumulative teaching.

F. Nakanishi, S. Okada, and H. Nakanishi, "Photoreaction of Long-Chain Mono n-Alkyl Esters of p-Phenylenediacrylic Acid in Multilayer Films", *Polymer Communications,* Vol. 27, August 1986, pp. 238 and 239, reports the formation of LB films with mono alkyl esters of p-phenylenediacrylic acid followed by UV exposure. While some degree of insolubilization was reported by exposure, solubility of the exposed film, particularly in multilayer assemblies was reported. The formation of dimers, trimers, and possibly other oligomers as opposed to true crosslinked polymers is an explanation suggested for retained solubility.

H. Koch, A. Laschewsky, H. Ringsdorf, and K. Teng, "Photodimerization and Photopolymerization of Amphiphilic Cinnamic Acid Derivatives in Oriented Monolayers, Vesicles and Solution", *Makromol. Chem.,* Vol. 187, pp. 1843–1853 (1986), reports investigations of UV exposure of amphiphiles containing a single cinnamic acid chain or two cinnamic acid chains linked through a head group. The single cinnamic acid chain monomers reacted intermolecularly to form dimers. The dual cinnamic acid chain compounds reacted intramolecularly without any significant change in molecular weight and to some extent intermolecularly to produce dimers, oligomers, and possibly some polymers.

E. Elbert, A. Laschewsky, and H. Ringsdorf, "Hydrophilic Spacer Groups in Polymerizable Lipids: Formation of Biomembrane Models from Bulk Polymerized Lipids", *J. Am. Chem. Soc.,* Vol. 107, 1985, pp. 4134–4141, reports investigations of a variety of polymerizable lipids containing a poly(ethylene oxide) spacer group between a methacrylate reactive moiety and an amphiphilic structure consisting of two hydrophobic ligands joined through an amino nitrogen, a quaternized nitrogen, an ester, or a phosphate linking group. The formation of LB film assemblies is disclosed. UV exposure is reported to result in polymerization.

SUMMARY OF THE INVENTION

The present invention has as its purpose to provide articles having LB film assemblies capable of being patterned by differential exposure and development during their preparation. Further, the present invention has as its purpose to provide articles having LB film assemblies in which an oriented monomolecular layer is presented of improved structural integrity and stability.

In one aspect the present invention is directed to an article containing a Langmuir-Blodgett film assembly characterized in that the film assembly includes at least one oriented polymer layer of monomolecular thickness containing repeating units comprised of a hydrophilic group linking two hydrophobic groups each containing at least two crosslinking moieties.

DESCRIPTION OF PREFERRED EMBODIMENTS

The present invention is directed to articles containing on a support an LB film assembly containing at least one oriented polymer layer produced by the photo-crosslinking of monomers oriented by LB deposition containing a hydrophilic group linking two hydrophobic groups each containing at least two moieties which can be photoactivated to undergo a crosslinking reaction.

To appreciate better the structural requirements of the monomers, it is useful first to review LB film assembly techniques. Molecules which lend themselves to the formation of oriented monomolecular films by LB assembly techniques contain a hydrophilic portion, referred to as a head, and a hydrophobic portion, referred to as a tail. Since the molecules have both hydrophilic and hydrophobic portions, they are amphiphilic and are referred to as amphiphiles. A small amount of an amphiphile spread on the surface of a liquid forms a surface film of monomolecular thickness at the air-liquid interface. If the supporting liquid is a polar liquid, such as water, the hydrophilic group or head of each amphiphile is drawn into the liquid, while the hydrophobic group or tail is attracted to the non-polar, air side of the interface to hold the amphiphile at the surface of the supporting liquid body. If, instead of air a non-miscible, nonpolar liquid is substituted for air, the same result is achieved. When the surface of the supporting liquid is fully covered by a monomolecular layer, the result is spatial alignment of the amphiphiles on the surface of the supporting liquid.

If a support is slowly immersed in the film bearing liquid body or slowly withdrawn from it, an oriented monomolecular film is formed on the substrate. When the support is slowly withdrawn from the polar liquid, a Z-type LB deposition results in which the LB film is formed with the head nearer to the support than the tail. This arrangement can be schematically illustrated as follows:

where
  T is a hydrophobic group or tail and
  L is a hydrophilic group or head.

In a multilayer Z-type LB film assembly a head-to-tail stacking of the layers occurs when deposition occurs only on successive withdrawals from the polar liquid, as can be schematically illustrated by the following three layer Z-type LB film assembly:

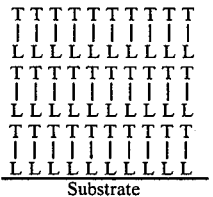

When the support is slowly immersed in the polar liquid, an X-type LB deposition results in which the LB film is formed with the tail of the film forming molecules nearer to the support than the head. This arrangement can be schematically illustrated as follows:

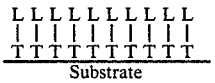

In a multilayer X-type LB film assembly a tail-to-head inverted stacking of the layers occurs when deposition occurs only on successive immersions in the polar liquid, as can be schematically illustrated by the following three layer X-type LB film assembly:

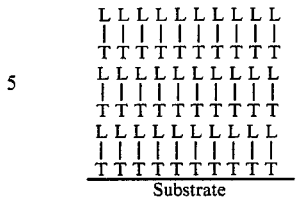

While multilayer X-type and Z-type LB film assemblies are both within the capabilities and contemplation of the present invention, it is to be noted that in both arrangements at layer interfaces a hydrophilic group is located immediately adjacent a hydrophobic group. This has been recognized in the art as a relationship that can contribute to layer instability. While the polymerization of each individual layer according to the teachings of this invention reduces the instability of multilayer X-type and Z-type LB film assemblies, to avoid the necessity of juxtaposing hydrophobic and hydrophilic groups it is preferred to form multilayer LB film assemblies by Y-type LB deposition in which successive layers are deposited alternately by substrate withdrawal from and immersion in the polar liquid. The more stable head-to-head and tail-to-tail stacking arrangement can be schematically illustrated by the following three layer Y-type LB film assembly:

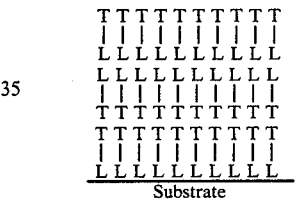

The monomers contemplated for use in forming oriented crosslinked polymer layers of monomolecular thickness in the articles of this invention are amphiphiles. They contain a hydrophilic group or head linking two hydrophobic groups or tails. They can be oriented like the simple L-T amphiphile structures described above, but differ in that the single tail T is elaborated into two separate tails $T^1$ and $T^2$. The monomers can be represented by Formula I:

where
  L is a hydrophilic linking group and
  $T^1$ and $T^2$ are hydrophobic groups each containing at least two moieties which can be photoactivated to undergo a crosslinking reaction.

The hydrophilic group can be chosen from among a variety of known divalent polar groups. Since a number of polar groups are available to choose among, selection is usually based on synthetic convenience.

In one preferred form the hydrophilic group is a phosphate group forming monomers which can be represented by Formula II:

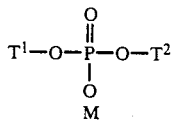
(II)

where

M is hydrogen, lower alkyl (e.g. from 1 to 3 carbon atoms), or a cation, such as an ammonium or alkali metal cation; and $T^1$ and $T^2$ are hydrophobic groups as previously defined.

In another preferred form the hydrophilic group is a ammonium group forming monomers which can be represented by Formulae III, IV, and V:

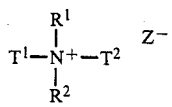
(III)

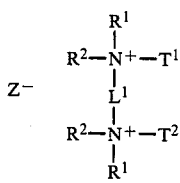
(IV)

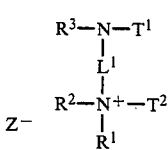
(V)

where $L^1$ is an optionally substituted divalent hydrocarbon substituent;

$R^1$ and $R^2$ are independently in each occurrence optionally substituted hydrocarbon quaternizing substituents;

$R^3$ is hydrogen or an optionally substituted hydrocarbon substituent;

$T^1$ and $T^2$ are hydrophobic groups as previously defined; and

Z represents one or more charge balancing counter ions.

$R^1$, $R^2$, and $R^3$ can be any synthetically convenient hydrocarbon substituents compatible with the desired hydrophilic character of the ammonium moiety. In preferred forms $R^1$, $R^2$, and $R^3$ independently take the form of lower alkyl groups. The lower alkyl groups can in turn be substituted with common modifying groups, such as aryl, halo, hydroxy, alkoxy, and aryloxy, where the alkyl moieties in each occurrence preferably contain 1 to 3 carbon atoms (i.e., methyl, ethyl, n-propyl, or i-propyl) and the aryl moieties contain 6 to 10 carbon atoms (e.g., phenyl or naphthyl). In another preferred form $R^1$ and $R^2$ together represent carbon and optionally oxygen atoms completing a 4 to 7 member ring (e.g., an azetidine, pyrrole, pyrroline, pyrrolidine, morpholine, or azepine ring).

The charge balancing counter ions Z can be provided by any convenient anion. The counter ion can be divalent or monovalent. In one contemplated form the counter ion Z can be a substituent of $R^1$, $R^2$, or $R^3$ so that a zwitterionic structure is formed.

While in the foregoing monomers the phosphate and ammonium moieties form the entire hydrophilic group L, in varied forms the ammonium and phosphate moieties can be combined with other polar moieties to form the hydrophilic group. This is illustrated by the complex lipids of Formulae VI and VII:

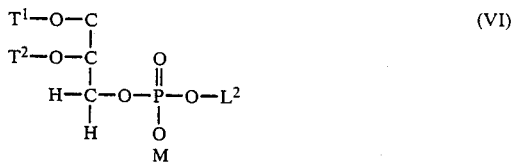
(VI)

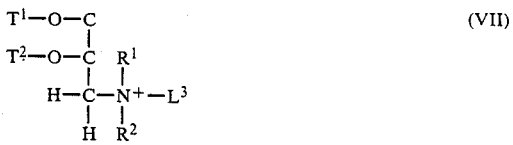
(VII)

where $L^2$ is a polar group, $L^3$ is alkyl of from 1 to 3 carbon atoms or a polar group, and M, $R^1$, $R^2$, $T^1$ and $T^2$ are as previously defined.

Any synthetically convenient polar group known to be useful in forming complex lipids can be employed. $L^2$ or $L^3$ can, for example, take the form $-(CH_2)_2N^+H_3$, $-(CH_2)_2N^+(CH_3)_3$ (a choline residue), $-CH_2CH(NH_2)-C(O)OM$ (a serine residue), where M is a previously defined, or alkylene oxide, such as $-(CH_2CH_2O)_xOR^4$, where x is 2 to 20 and $R^4$ is hydrogen or lower alkyl—e.g., alkyl of from 1 to 3 carbon atoms, similarly as $R^1$ described above.

Still other divalent polar linking groups can be employed, if desired. For example, Elbert et al, cited above, suggests the equivalence of ammonium, phosphate, and succinate polar moieties in polymerizable lipids.

The hydrophobic groups $T^1$ and $T^2$ completing the amphiphile monomers each contain at least two moieties which can be photoactivated to undergo a crosslinking reaction and one or a combination of moieties which individually or collectively impart the desired degree of hydrophobicity.

Hydrophobic groups can be conveniently synthesized in the form of linear sequences of moieties, as illustrated by Formula VIII:

(VIII)

where $D^1$ is a terminal hydrophobic moiety;

$D^2$, and $D^3$ are divalent linking moieties;

$E^1$ and $E^2$ are moieties chosen to provide photocrosslinking sites;

p, q, and r can be either the integer 1 or zero, provided that least one of p, q, and r is 1; and $D^1$, $D^2$, and $D^3$ collectively provide at least 7, preferably at least 10, and optimally at least 18 aliphatic carbon atoms.

In the preferred form of the invention $E^1$ and $E^2$ each take the form of activated ethylene moieties. As herein employed, the term "activated ethylene moiety" indicates an α-alken-1,2-diyl group capable of undergoing a saturating addition reaction upon exposure to electromagnetic radiation. Response to radiation is imparted by one or more activating groups. While $E^1$ and $E^2$ in every instance each provide a separate site of ethylenic unsaturation capable of acting as a photocrosslinking site, when $E^1$ and $E^2$ are next adjacent groups (that is, q is zero so that $D^2$ is absent), contiguously bonded activating groups can be shared.

In one preferred form an activated vinyl moiety suitable for the formation of $E^1$ or $E^2$ is illustrated by Formula IX:

where
Ac is activating moiety;
$Ar^1$ is an aromatic moiety;
$R^5$ is hydrogen, halogen, or alkyl of from 1 to 6 carbon atoms, preferably hydrogen or methyl; and y is zero or 1.

Either or both of $E^1$ and $E^2$ can take the form shown in Formula IX, whether the groups are next adjacent or separated by the intermediate linking group $D^2$. When p is 0 and $D^1$ is therefore not present, $Ar^1$ is, of course, a monovalent aromatic moiety rather than a divalent aromatic moiety as shown.

When $E^1$ and $E^2$ are next adjacent groups, simplified structures are possible in which one or both of $Ar^1$ and Ac are shared by the adjacent $E^1$ and $E^2$ groups. Stated another way, a separate Ac and $Ar^1$ group are not required for each of $E^1$ and $E^2$ when they are next adjacent groups. $E^1$ and $E^2$ together can in specifically preferred forms of the invention be represented by Formulae X and XI:

and

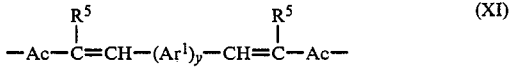

where Ac, $Ar^1$, $R^4$, and y are as previously defined.

The activating moiety Ac can take the form of a carbonyloxy, amido, sulfinyl, sulfonyl, sulfonylamido, or sulfonate moiety. Preferred combinations of these activating moieties and an adjacent α-alken-1,2-diyl moiety are illustrated by Formulae XII through XIV:

where
$R^4$ is as previously defined, preferably hydrogen or methyl;
s is the integer 0 or 1;
X is oxygen or $-NR^6-$; and $R^6$ is hydrogen or alkyl of from 1 to 3 carbon atoms.

$Ar^1$ is preferably in each occurrence a carbocyclic aromatic moiety containing from 6 to 10 ring carbon atoms. It is possible for $Ar^1$ to be a monovalent terminal group, such as phenyl or naphthyl, but in most instances $Ar^1$ is a divalent group, such as phenylene or naphthylene. When $Ar^1$ is a phenylene or naphthylene group, it is most preferably a 1,4-phenylene or 1,4-naphthylene group.

Although the foregoing activated ethylene moieties are preferred, other variations in their structural form are contemplated. Referring to Formula VIII, when the activated ethylene moiety is a terminal moiety—that is, p is 0 and $D^1$ is therefore absent, $E^1$ can take a form illustrated by Formula XV:

where
Ac and $R^5$ are as previously defined.

In another form $E^1$ as a terminal moiety can be represented by Formula XVI:

where
Ac and $Ar^1$ are as previously defined.

$D^1$, $D^2$, and $D^3$ must collectively impart sufficient hydrophobicity to render the molecule amphiphilic. When $D^1$, $D^2$, and $D^3$ together provide at least 7 aliphatic carbon atoms, a minimum degree of hydrophobicity can be imparted to the molecule. It is generally preferred that these groups together provide at least 10 and optimally at least 18 aliphatic carbon atoms. While the number of aliphatic carbon atoms provided by these groups can range to 30 or 40 or beyond, it is generally preferred to limit the molecular bulk of the groups to that needed to impart hydrophobicity. Therefore, $D^1$, $D^2$, and $D^3$ together preferably contain 25 or fewer aliphatic carbon atoms.

In one preferred form of the amphiphiles, polar groups in the tail portion of the molecule, such as activating groups in the crosslinking moieties, are located as close to the hydrophilic linking group as possible while the terminal group $D^1$ is an alkyl group containing all or most of the aliphatic carbon atoms relied upon hydrophobicity. In this way, the amphiphile becomes progressively more oleophilic in a head-to-tail direction. In this form $D^1$ in each of the tails can contain from 7 to 25 carbon atoms, preferably from about 10 to 18 carbon atoms.

In some of the tail configurations described above, the crosslinking moiety $E^1$ is the terminal group of the tail. In this instance, when $E^1$ and $E^2$ are not immediately adjacent (that is, q=1 in Formula VIII), $D^2$ and $D^3$ in each of the tails are divalent alkylene groups, where the alkylene groups $D^2$ and $D^3$ together in each tail provide 7 to 25, preferably 10 to 18, carbon atoms. When $E^1$ and $E^2$ are next adjacent groups so that the linking group $D^2$ is absent, the requisite hydrophobicity can be supplied by $D^1$ alone or some combination of $D^1$ and $D^3$. Since both $D^1$ and $D^2$ can be omitted in some structural forms, it is apparent that $D^3$ in each of the tails can be a divalent alkylene, $-C_nH_{2n}-$, where n is 7 to 25, preferably 10 to 18.

In specifically preferred molecular constructions of the molecular tails, $D^1$ is present as the sole or predominant hydrophobic group, the crosslinking moieties $E^1$ and $E^2$ are present in one of the two simplified forms shown in Formulae X and XI and $D^3$ is chosen solely for synthetic convenience without regard to whether it is hydrophobic or hydrophilic in character.

Specific monomers contemplated for use in constructing LB film assemblies satisfying the requirements of the invention are set forth below in Table I.

TABLE I

A-1
$$\left[C_4H_9-O-\overset{O}{\underset{\|}{C}}-CH=CH-\underset{}{\bigcirc}-CH=CH-\overset{O}{\underset{\|}{C}}-O-(CH_2)_6-O\right]_2 \overset{O}{\underset{\|}{P}}-OH$$

A-2
$$Br^{\ominus}$$
$$H_3C-\overset{CH_3}{\underset{|}{\overset{+}{N}}}-T^1$$
$$\underset{|}{(CH_2)_3}$$
$$H_3C-\overset{|}{\underset{+|}{N}}-T^2$$
$$\underset{}{CH_3}$$
$$Br^{\ominus}$$

$T^1 = T^2 = -(CH_2)_{11}-O-\overset{O}{\underset{\|}{C}}-CH=CH-\underset{}{\bigcirc}-CH=CH-\overset{O}{\underset{\|}{C}}-OC_2H_5$ A-3
$$Br^{\ominus}$$
$$H_3C-\overset{CH_3}{\underset{|}{\overset{+}{N}}}-T^1$$
$$\underset{|}{(CH_2)_3}$$
$$H_3C-\overset{|}{\underset{+|}{N}}-T^2$$
$$\underset{}{CH_3}$$
$$Br^{\ominus}$$

$T^1 = T^2 = -(CH_2)_6-O-\overset{O}{\underset{\|}{C}}-CH=CH-CH=CH-(CH_2)_{16}-CH_3$ A-4
$$T^1-O-CH_2$$
$$T^2-O-\overset{|}{CH}$$
$$H_2\overset{|}{C}-O-\overset{O}{\underset{\underset{O^\ominus}{\|}}{P}}-O-CH_2CH_2-\overset{CH_3}{\underset{\underset{CH_3}{|}}{\overset{+}{N}}}-CH_3$$

$T^1 = T^2 = C_2H_5-CH=CH-\underset{}{\bigcirc}-CH=CH-\overset{O}{\underset{\|}{C}}-O-(CH_2)_9-\overset{O}{\underset{\|}{C}}-$ A-5
$$T^1-O-CH_2$$
$$T^2-O-\overset{|}{CH}$$
$$H_2\overset{|}{C}-O-\overset{O}{\underset{\underset{O^\ominus}{\|}}{P}}-O-CH_2CH_2\overset{+}{N}H_3$$

$T^1 = T^2 = H_3-(CH_2)_{12}-CH=CH-CH=CH-\overset{O}{\underset{\|}{C}}-O-(CH_2)_{11}-\overset{O}{\underset{\|}{C}}-$ A-6
$$Br^{\ominus} \quad \underset{CH_3}{\overset{CH_3}{\diagdown}}\overset{+}{N}-\left[(CH_2)_{11}-O-\overset{O}{\underset{\|}{C}}-CH=CH-\underset{}{\bigcirc}-CH=CH-\overset{O}{\underset{\|}{C}}-O-C_2H_5\right]_2$$

A-7
$$Br^{\ominus} \quad \underset{C_2H_5}{\overset{C_2H_5}{\diagdown}}\overset{+}{N}-\left[CH_2CH_2-O-\overset{O}{\underset{\|}{C}}-CH=CH-\underset{}{\bigcirc}-CH=CH-\overset{O}{\underset{\|}{C}}-O-C_4H_9\right]_2$$

TABLE I-continued

A-8

$$\overset{CH_3}{\underset{CH_3}{Br^{\ominus} + N^+}} \left[ -(CH_2)_{11}-O-\overset{O}{\underset{\|}{C}}-CH=CH-CH=CH-CH_3 \right]_2$$

A-9

$$\left[ CH_3(CH_2)_{12}CH=CH-CH=\overset{O}{\underset{\|}{C}}-O-(CH_2)_8-O \right]_2 \overset{O}{\underset{OH}{\|}}P$$

A-10

$$\left[ CH_3(CH_2)_7-O-\overset{O}{\underset{\|}{C}}-CH=CH-\phantom{x}\bigcirc\phantom{x}-CH=CH-\overset{O}{\underset{\|}{C}}-NH(CH_6)-O \right]_2 \overset{O}{\underset{OH}{\|}}P$$

A-11

$$\left[ \phantom{x}\bigcirc\phantom{x}-(CH_2)_3-NH-\overset{O}{\underset{\|}{C}}-CH=CH-\phantom{x}\bigcirc\phantom{x}-CH=CH-\overset{O}{\underset{\|}{C}}-NH(CH_2)_6O \right]_2 \overset{O}{\underset{OH}{\|}}P$$

A-12

$$\left[ CH_3-CH=CH-CH=CH-\overset{O}{\underset{\|}{C}}-O(CH_2)_{12}-O \right]_2 \overset{O}{\underset{OH}{\|}}P$$

A-13

$$\left[ CH_3-(CH_3)_{12}-CH=CH-CH=CH-CH=CH-\overset{O}{\underset{\|}{C}}-O(CH_2)_{16}-O \right]_2 \overset{O}{\underset{OH}{\|}}P$$

A-14

$$\left[ \underset{\phi}{\overset{\phi}{\triangle}}\underset{H}{\overset{\overset{O}{\|}}{C}}-O(CH_2)_{11}-O-\phantom{x}\bigcirc\phantom{x}-CH=CH-\overset{O}{\underset{\|}{C}}-O(CH_2)_8-O \right]_2 \overset{O}{\underset{OH}{\|}}P$$

$\phi$ = phenyl

A-15

$$\left[ \underset{CH_2}{\overset{CH_3}{\diagdown}}\overset{O}{\underset{\|}{C}}-O(CH_2)_{11}-O-\phantom{x}\bigcirc\phantom{x}-CH=CH-CH=CH-\overset{O}{\underset{\|}{C}}-O(CH_2)_4-O \right]_2 \overset{O}{\underset{OH}{\|}}P$$

A-16

$$\left[ CH_3(CH_3)_{20}-CH=CH-CH=CH-\overset{O}{\underset{\|}{C}}-O(CH_2)_6-O-\phantom{x}\bigcirc\phantom{x}-CH=CH-\overset{O}{\underset{\|}{C}}-O(CH_2)_4-O \right]_2 \overset{O}{\underset{OH}{\|}}P$$

A-17

$$\left[ CH_3(CH_2)_{12}-O-\overset{O}{\underset{\|}{C}}-CH=CH-\phantom{x}\bigcirc\phantom{x}-CH=CH-\overset{O}{\underset{\|}{C}}-O(CH_2)_2-O-\phantom{x}\bigcirc\phantom{x}-CH=CH-\overset{O}{\underset{\|}{C}}-O(CH_2)_2-O \right]_2 \overset{O}{\underset{OH}{\|}}P$$

A-18

$$\left[ \underset{\phi}{\overset{\phi}{\triangle}}\underset{H}{\overset{\overset{O}{\|}}{C}}-O(CH_2)_2-O-\overset{O}{\underset{\|}{C}}-CH=CH-\phantom{x}\bigcirc\phantom{x}-CH=CH-\phantom{x}\bigcirc\phantom{x}-CH=CH-\overset{O}{\underset{\|}{C}}-NH(CH_2)_2-O \right]_2 \overset{O}{\underset{OH}{\|}}P$$

$\phi$ = phenyl

TABLE I-continued

A-19
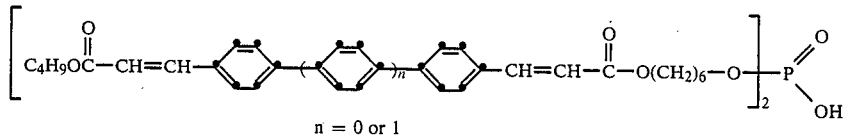
n = 0 or 1

A-20
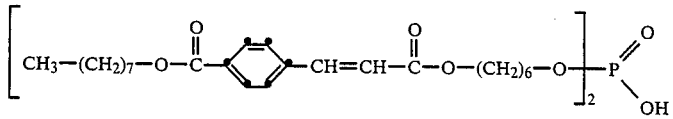

A-21
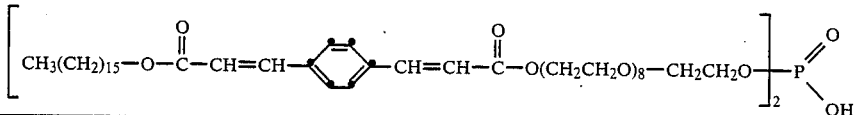

The amphiphilic monomers can be deposited on a support to form an X, Y, or Z-type LB film employing conventional film assembly techniques. The techniques disclosed by Stroeve et al, Garito et al, Lieser et al, and Nakanishi et al, cited above, are illustrative of conventional film assembly techniques.

After one or more oriented monomer layers have been deposited by LB assembly techniques, the deposited monomers are exposed to electromagnetic radiation capable of stimulating crosslinking. The advantage of photocrosslinking the monomers is that the risk of disruption of the monomer layers created by bringing another material into contact with the LB monomers is eliminated. By choosing wavelengths of electromagnetic radiation which can be absorbed by the the monomers direct crosslinking can be achieved without any need for auxiliary agents such as polymerization initiators and photosensitizers. In preferred forms of the invention the monomers are transparent to visible radiation and exhibit peak absorption in the ultraviolet portion of the spectrum. Electromagnetic radiation supplied to the monomers for crosslinking preferably includes wavelengths at or near the peak absorption wavelength of the monomers.

The least opportunity for monomer layer disruption is presented when photocrosslinking is undertaken following deposition of each monomer layer. In many instances, however, it may be more convenient to deposit several monomer layers before undertaking photocrosslinking.

The substrates on which the LB films are formed can take any of a wide variety of conventional forms. Any substrate which presents a smooth surface for deposition and which does not react with the monomers can be employed. Substrates of metal, glass, ceramic oxides, semiconductors and organic polymers are specifically contemplated. Semiconductor substrates, such as monocrystalline silicon or III-V compounds (e.g., gallium arsenide, gallium aluminum arsenide, or gallium phosphide), are typically first passivated with one or more surface passivant layers (e.g., silicon dioxide, silicon nitride, or glass). Organic polymer supports can take the form of photoresist coatings or film supports. Typical of useful polymeric film supports are films of cellulose nitrate and cellulose esters such as cellulose triacetate and diacetate, polystyrene, polyamides, homo- and co-polymers of vinyl chloride, poly(vinyl acetal), polycarbonate, homo- and co-polymers of olefins, such as polyethylene and polypropylene, and polyesters of dibasic aromatic carboxylic acids with divalent alcohols, such as poly(ethylene terephthalate). The composition or construction of the substrate beneath the surface at which formation of the LB layer assembly is formed is immaterial to the practice of the invention.

Since the oriented monomers are located on the support by moving the support through a liquid interface, the oriented monomers are deposited over the entire exterior surface of the support. In practice an LB film assembly is often desired on only a limited areal extent of the support. To pattern the crosslinked LB assembly forming the final coating, patterned exposure to crosslinking electromagnetic radiation is undertaken followed by washing. Whereas organic monomers, dimers, trimers, oligomers, and linear polymers exhibit solubility in common organic solvents, crosslinked polymers are insoluble. Useful organic solvents for monomer removal can be selected from among such common organic solvents as alcohols, ethers, tetrahydrofuran, dimethylformamide, dimethylsulfoxide, chloroform, dichloromethane, acetonitrile, and acetone. Since monomer removal by washing is not undertaken until after crosslinking has occurred, there is minimal risk of damage to the retained crosslinked LB film. Washing to remove monomer from unwanted areas on the support can be performed after each layer is photocrosslinked. In most instances it is convenient to photocrosslink all or several of the layers simultaneously. Even when there is more than one photocrosslinking step undertaken, it is generally convenient to defer washing until after all layers have been deposited and photocrosslinked.

The articles produced by the practice of the invention can serve any known utility for LB film assemblies. In a specifically preferred form of the invention optical articles are produced. Specifically, transparent LB film assemblies are contemplated capable of acting as waveguides for the transmission of electromagnetic radiation. For example, the LB film assemblies can be used to direct light between conventional optical articles, such as prisms, light conducting fibers, lasers, photodiodes, and the like.

EXAMPLES

The invention can be better appreciated by reference to the following examples:

EXAMPLE 1

Bis[6-(4-butoxycarbonylvinylcinnamoyloxy)hexyl]-phosphate (A-1)

Freshly distilled phosphorous oxychloride (1.26 g, 8.1 mmoles) in benzene (10 ml) was stirred and cooled to 0° C. After the addition of pyridine (1.26 g, 16.2 mmoles) in benzene (10 ml) at 0° C., a solution of butyl 6-hydroxyhexyl 3,3'-(1,4-phenylene)-bisacrylate (6.0 g, 16.2 mmoles) dissolved in benzene (130 ml) was added dropwise at 0° C. The mixture was stirred at ambient temperature for 16 hours and then heated at 40°–50° C. for 1.5 hours. The reaction was cooled to 0°–10° C., filtered, and the solvent removed. Water was added to the residue (100 ml) and it was heated at reflux for 45 minutes. After heating, the reaction was cooled to room temperature and the aqueous mixture was extracted with 200 ml of dichloromethane. The extraction was repeated so that it was performed four times. The combined organic solution was dried over anhydrous magnesium sulfate, filtered, and the solvent removed. The residue was dissolved by heating with acetone (50 ml) and then cooled in a freezer. The white solid was collected: Yield 4.0 g (60%) mp 95°–99° C.

Anal. calculated for $C_{44}H_{59}O_{12}P$: C, 65.2; H, 7.3; P, 3.8. Found C, 66.8; H, 7.3; P, 3.8. NMR(CDCl$_3$) 0.9 (t, 6H, CH$_3$), 1.1–1.9 (m, 24H, CH$_2$'s), 4.1 (m, 12H, CH$_2$—O), 6.35 (d, 4H, C=CH—C=O), 7.6 (d, 4H, =CH—Ph—CH=), 7.45 (s, 8H, Ph H's).

EXAMPLE 2 (CONTROL)

6-(4'-Butoxycarbonylvinylcinnamoyloxy)hexyl ethyl phosphate

Freshly distilled phosphorous oxychloride (1.5 g, 10 mmoles) in benzene (10 ml) was stirred and cooled to 0° C. After the addition of pyridine (0.8 g, 10 mmoles) in benzene (10 ml) at °C., a solution of butyl 6-hydroxyhexyl 3,3'-(1,4-phenylene)bisacrylate (3.74 g, 10 mmoles) in benzene (100 ml) was added dropwise at 0° C. and stirred at room temperature for 16 hours. The next day the reaction was cooled to 0° C. and pyridine (0.8 g, 10 mmoles) in benzene (10 ml) was added, followed by ethanol (0.8 g, 20 mmoles) in benzene (15 ml) at 0° C. The reaction was stirred an additional 16 hours at room temperature and then heated at 40°–50° C. for 30 minutes, cooled to 0° C., filtered, and the solvent removed. Water was added to the residue (100 ml) and it was heated at reflux for 45 minutes. The reaction was cooled and the aqueous mixture was extracted with 200 ml of dichloromethane. The extraction was repeated so that it was performed four times. The combined organic solution was washed with 3% HCl solution (100 ml), saturated NaCl solution (100 ml), and dried over anhydrous magnesium sulfate, filtered, and the solvent removed. To the residue (oil) was added acetone (20 ml) and the mixture filtered. After two days a solid crystallized which was collected: Yield 15% mp 50°–52° C.

Anal. calculated for $C_{24}H_{35}O_8P$: C, 59.7; H, 7.3; P, 6.4. Found: C, 58.9; H, 6.4; P, 6.3.

EXAMPLE 3 (CONTROL)

4'-Octadecyloxycarbonylvinylcinnamic acid

Bis octadecyl 3,3'-(1,4-phenylene)bis acrylate (2.5 g, 3.45 mmoles) was dissolved in 1-octanol (20 g) with heat. This was added to a hot solution of 1-octdecanol (10 g) and sodium hydroxide (0.14 g, 3.45 mmoles). The mixture was heated at 100° C. for six hours and then filtered. The solid was dissolved in hot water (200 ml) and 10% HCl solution added to produce a pH of 4. The solid was filtered and is soluble in tetrahydrofuran.

Anal. calculated for $C_{30}H_{46}O_4P$: C, 76.6; H, 9.9. Found: C, 76.1; H, 9.7.

EXAMPLE 4

Bis[8-(octadeca-2,4-dienoyl)octyl]-phosphate (A-9)

Freshly distilled phosphorous oxychloride (1.26 g, 8.1 mmoles) in benzene (15 ml) was stirred and cooled to 0° C. After the addition of pyridine (1.26 g, 16.2 mmoles) in benzene (15 ml) at 0° C., a solution of 8-(octadeca-2,4-dienoyl)octanol (6.8 g, 17.3 mmoles) in benzene (100 ml) was added dropwise at 0° C. The mixture was stirred at ambient temperature for 16 hours and then heated to 40°–50° C. for 1 hour. The reaction was cooled, filtered, and the solvent removed. Water was added to the residue (100 ml) and it was heated at reflux for 45 minutes. The reaction was cooled to room temperature and the aqueous mixture was extracted with 200 ml of dichloromethane. The extraction was repeated so that it was performed four times. The combined organic solution was washed twice with some of 4% HCl solution dried over anhydrous magnesium sulfate, filtered, and the solvent removed. The residue was dissolved in acetone (50 ml) and on cooling a solid precipitated. The white solid was collected: Yield 50% mp 73°–74° C.

Anal. calculated for $C_{52}H_{95}O_8P$: C, 71.0; H, 10.9; P, 3.5. Found: C, 71.0; H, 10.2; P, 3.9. NMR(CDCl$_3$) 0.9 (t, 6H, CH$_3$), 1.2–1.9 (m, 68H, CH$_2$'s), 2.2 (m, 4H, CH$_2$—CH=), 4.1 (m, 8H, CH$_2$—O), 5.74 (d, 2H, C=CH—C=O), 6.2 (m, 4H, CH=CH—CH$_3$), 7.1–7.4 (m, 2H, CH=C—C=O).

EXAMPLE 5 (CONTROL)

Docosanyl-2,4-dienoic acid

To 2,4-docosanyldienal (50 g, 0.156 mole) in tetrahydrofuran (400 ml) at 0°–5° C. was added a solution of sodium acetate (40 g, 0.48 mole) and acetic acid (40 g, 0.67 mole) in water (400 ml). To this mixture was added 2-methyl-2-butene (160 ml) and a solution of sodium chloride (60 g, 0.48 mole) in water (400 ml). The mixture was stirred vigorously for 1 hour and 45 minutes and then ether (400 ml) was added. The organic layer was separated and the aqueous solution was extracted 5 times with ether (200 ml). The combined organic extracts were dried over anhydrous magnesium sulfate, solvent removed and the residue recrystallized from hexane (150 ml). Yield 90% mp 83°–85° C.

EXAMPLE 6

All experiments to prepare and test Langmuir-Blodgett films described in this and the following examples were performed at an ambient laboratory temperature of approximately 20° C. Several drops of a solution of the compound in Example 1 dissolved in chloroform were spread onto the water surface of a Langmuir-Blodgett trough. The water contained $3 \times 10^{-4}$ molar cadmium chloride and $1 \times 10^{-4}$ molar sodium bicarbonate. Multivalent heavy metal ions such as cadmium are commonly added to the water from which Langmuir-Blodgett films of compounds containing complexing headgroups are deposited in order to form more cohesive and readily deposited films. After a short wait for solvent evaporation of approximately five minutes, the movable barrier of the trough was activated to slowly compress the film in the manner common to the technique of preparing films for Langmuir-Blodgett deposition. Compression to 30 dyne/cm (milliNewton/meter) surface pressure was achieved and maintained. A substrate consisting of a quartz plate coated with cadmium arachidate rendering its surface hydrophobic was slowly mechanically immersed through the monolayer at the air-water interface into the trough of the Langmuir-Blodgett film deposition apparatus. Deposition of material onto the substrate from the water surface was measured by electronically monitoring the change in position of the movable barrier as it maintained the preset constant surface pressure on the film. After immersion of the substrate the direction of movement was reversed and it was slowly withdrawn through the monolayer film at the air-water interface, resulting in the deposition of a second monolayer onto each face of the quartz plate. This cycle was repeated to build up the desired number of multilayers onto each face of the substrate in the Y deposition mode. Up to twenty layers were deposited, although generally ten layers were used for sample tests. Since the amount of material that was transferred from the water surface to the substrate at each immersion-withdrawal cycle remained essentially constant as more layers were deposited, more than twenty layers can clearly be deposited. An absorption spectrum of the sample was obtained by placing it in the sample chamber of a commercial spectrophotometer and scanning in the ultraviolet and visible range. An absorption band with peak absorption at 285 nanometers, due to the electronic absorption of the para-phenylenediacrylate chromophore, was observed. Maximum absorption was 0.20 absorbance units for ten layers deposited onto each face of the substrate. The sample was then placed in the beam of a high pressure mercury or xenon lamp emitting light of wavelengths greater than approximately 200 nanometers and specifically including wavelengths of less than 350 nanometers and was exposed for a time until the initial absorption had decreased to approximately half of the original value prior to exposure. An absorption spectrum of this photolyzed sample was then measured. The sample was then immersed into a container of solvent for a measured time, withdrawn, and allowed to dry. Thereupon another absorption measurement was made to determine the amount of material remaining in comparison to that prior to solvent treatment. Samples prepared and photolyzed in the above manner were tested in the following solvents: chloroform made acidic by exposure to hydrogen chloride gas, ethanol made acidic by the addition of a small amount of concentrated aqueous hydrochloric acid, and Kodak ® 934 microlithographic developer. It was found to be necessary to make the organic solvents acidic since without this procedure all the films investigated, whether photolyzed or not, or even when composed of unreactive materials such as arachidic acid, were found to be insoluble in these solvents. This was determined to be due to the presence of the cadmium ions in the water, presumably through the formation of insoluble salts with the amphiphiles. In each case solvent immersion of up to five minutes resulted in no decrease in the absorption. In fact small increases in absorption were seen. Longer solvent treatment was not investigated. Samples photolyzed for longer times yielded similar results. For samples prepared and tested in the identical manner with the omission of the photolysis greater than 90% of the original absorption intensity was lost upon solvent treatment within one minute in each of these solvents. Thus exposure of Langmuir-Blodgett films of this compound causes a photochemical reaction which renders these films essentially insoluble to the test solvents.

EXAMPLE 7 (CONTROL)

When the procedure of Example 6 was repeated using the compound of Example 2 stable films did not form at the air water interface as shown by the fact that the surface pressure did not rise above 5.0 milliNewtons/meter as the surface area was decreased to less than ten Angstrom (A) per molecule of this compound spread onto the water surface in chloroform solution. Thus Langmuir-Blodgett films of this compound could not be deposited under the described conditions.

EXAMPLE 8 (CONTROL)

Langmuir-Blodgett films containing multilayers of the compound in Example 3 were prepared in the same manner as described in Example 6. Absorption spectra, exposures, and solubility were measured as described in Example 6. Peak absorption of a sample containing ten layers on each surface of the substrate was 0.18 absorbance units at 275 nanometers prior to exposure. Solubility was tested in the same solvents as Example 6. In contrast to Example 6, the absorbance of the sample tested in the acidic ethanol was reduced by 88% and the absorbance of the sample teated in the acidic chloroform was reduced by greater than 90% in comparison to the value following exposure within one minute of the solvent immersion. Unexposed samples also showed a reduction of greater than 90% of the original absorption intensity upon solvent treatment within one minute of immersion in each of these solvents. Neither exposed nor unexposed samples of this compound were appreciably soluble in the Kodak ® 934 developer (initial absorption decreased by less than 10%). Thus exposure of Langmuir-Blodgett films of this compound causes a photochemical reaction but this reaction does not result in an appreciable decrease in the solubility of the films to the test solvents.

EXAMPLE 9

Langmuir-Blodgett films containing multilayers of the compound in Example 4 were prepared in the same manner as described in Example 6. Absorption spectra were measured as described in Example 6. Exposures were made using a low pressure mercury lamp emitting at a wavelength of 254 nanometers. Initial peak absorption of a sample with six layers on each surface of the substrate was 0.13 absorbance units at 235 nanometers prior to photolysis. This was reduced by approximately one-half by exposure. Solubility was tested in the acidified chloroform and ethanol solvents described in Example 6. Immersion of the exposed sample into the ethanol solvent for up to one minute reduced the absorption measured after photolysis by less than 10%. Immersion of an unexposed sample into the ethanol solvent for up to one minute reduced the initial absorption by greater than 90%. Immersion of an exposed or an unexposed sample into the chloroform solvent reduced the absorption by greater than 90% within one minute of immersion. Thus exposure of Langmuir-Blodgett films of this compound causes a photochemical reaction which renders the film essentially insoluble to acidic ethanol but not to acidic chloroform.

EXAMPLE 10 (CONTROL)

Langmuir-Blodgett films containing multilayers of the compound in Example 5 were prepared in the same manner as described in Example 6. Absorption spectra were measured as described in Example 6. Exposures were made using a low pressure mercury lamp emitting at a wavelength of 254 nanometers. Initial peak absorption of a sample with six layers on each surface of the substrate prior to photolysis was 0.15 absorbance units at 220 nanometers. Photolytic exposure was continued until the initial absorption was decreased by approximately one-half. Solubility was tested in the acidified chloroform and ethanol solvents described in Example 6. Immersion of exposed samples into the ethanol or chloroform solvent reduced the absorption measured after photolysis by greater than 90%. Immersion of unexposed samples into these solvents similarly reduced the films of this compound. Exposure causes a photochemical reaction but this reaction does not result in an appreciable decrease in the solubility of the films to the test solvents.

The invention has been described in detail with particular reference to preferred embodiments thereof, but it will be understood that variations and modifications can be effected within the spirit and scope of the invention.

What is claimed is:

1. An article containing a Langmuir-Blodgett film assembly characterized in that said film assembly is transparent and includes at least one oriented polymer layer of monomolecular thickness containing repeating units derived from a monomer of the structure:

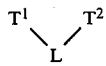

where
L is a hydrophilic linking group and
$T^1$ and $T^2$ are hydrophobic groups each of which satisfy the structure:

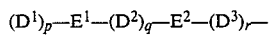

where
$D^1$ is a terminal hydrophobic moiety;
$D^2$, and $D^3$ are divalent linking moieties;
$E^1$ and $E^2$ are activated ethylene moieties chosen to provide photocrosslinking sites;
p, q, and r can be either the integer 1 or zero, provided that least one of p, q, and r is 1; and
$D^1$, $D^2$, and $D^3$ collectively provide in each of $T^1$ and $T^2$ at least 7 aliphatic carbon atoms.

2. An article according to claim 1 further characterized in that L is comprised of a phosphate group.

3. An article according to claim 2 further characterized in that the phosphate group satisfies the structure:

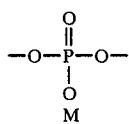

where

M is hydrogen, lower alkyl, or a cation.

4. An article according to claim 3 further characterized in that the monomer is a phospholipid.

5. An article according to claim 4 further characterized in that L satisfies the structure:

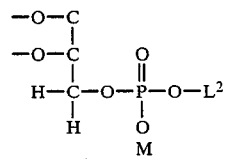

where
$L^2$ is a polar group and
M is hydrogen, lower alkyl, or a cation.

6. An article according to claim 1 further characterized in that L is comprised of an ammonium group.

7. An article according to claim 6 further characterized in that L satisfies the structure:

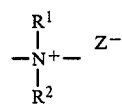

where
$R^1$ and $R^2$ are optionally substituted hydrocarbon quaternizing substituents and
Z is a charge balancing counter ion.

8. An article according to claim 6 further characterized in that L satisfies the structure:

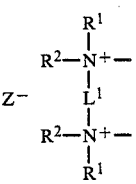

or

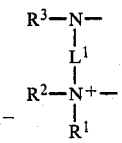

where
$L^1$ is an optionally substituted divalent hydrocarbon substituent;
$R^1$ and $R^2$ are independently in each occurrence optionally substituted hydrocarbon quaternizing substituents;
$R^3$ is hydrogen or an optionally substituted hydrocarbon substituent; and
Z represents one or more charge balancing counter ions.

9. An article according to claim 1 further characterized in that $D^1$, $D^2$, and $D^3$ collectively provide in each of $T^1$ and $T^2$ at least 10 aliphatic carbon atoms.

10. An article according to claim 9 further characterized in that $D^1$, $D^2$, and $D^3$ collectively provide in each of $T^1$ and $T^2$ at least 18 aliphatic carbon atoms.

11. An article according to claim 1 further characterized in that at least one of $E^1$ and $E^2$ satisfies the structure:

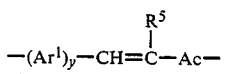

where
Ac is activating moiety;
$Ar^1$ is an aromatic moiety;
$R^5$ is hydrogen, halogen, or alkyl of from 1 to 6 carbon atoms; and
y is zero or 1.

12. An article according to claim 1 further characterized in that q is zero and $E^1$ and $E^2$ together satisfy the structure:

where
Ac is activating moiety.

13. An article according to claim 1 further characterized in that q is zero and $E^1$ and $E^2$ together satisfy the structure:

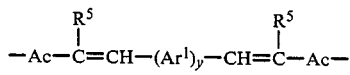

where
Ac is activating moiety;
$Ar^1$ is an aromatic moiety;
$R^5$ is hydrogen, halogen, or alkyl of from 1 to 6 carbon atoms; and
y is zero or 1.

14. An article according to claim 1 further characterized in that p is zero and $E^1$ satisfies the structure:

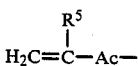

or

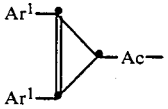

where
Ac is activating moiety and
$Ar^1$ is an aromatic moiety.

15. An optical article comprised of a support and, coated on the support,
a multilayer Langmuir-Blodgett transparent film assembly comprised of a plurality of layers formed by a crosslinked polymer having repeating units derived from oriented monomers of the structure:

where
L is an ammonium or phosphate hydrophilic linking group and
$T^1$ and $T^2$ are hydrophobic groups each containing each satisfying the structure:
$D^1-E^1-E^2-(D^3)_r-$ where
$D^1$ is an alkyl group;
$D^3$ is an alkylene group;
r is zero or 1;
$D^1$ and $D^3$ together contain from 7 to 25 carbon atoms;
$E^1$ and $E^2$ together satisfy the structure:

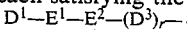

or

where
Ac is an activating moiety chosen from the class consisting of carbonyloxy, amido, sulfinyl, sulfonyl, sulfonamido, and sulfonate moieties;
$Ar^1$ is 1,4-phenylene moiety;
$R^5$ is hydrogen or methyl;
y is zero or 1.

16. An optical article according to claim 15 further characterized in that the Langmuir-Blodgett film assembly is a Y type film assembly.

17. An optical article comprised of
a support and, coated on the support,
a multilayer Langmuir-Blodgett transparent film assembly comprised of a plurality of layers formed by a crosslinked polymer having repeating units derived from oriented monomers chosen from the group consisting of:

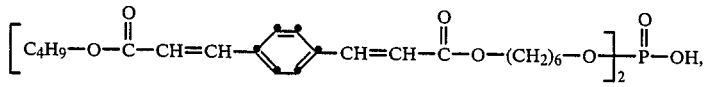   1

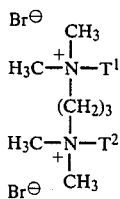   2

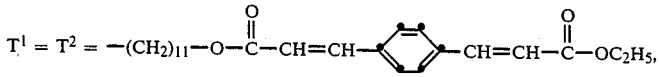

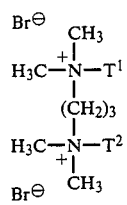
3
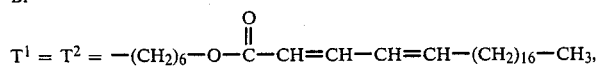
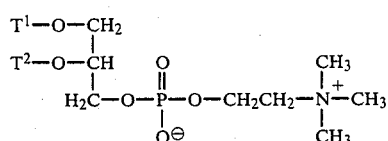
4
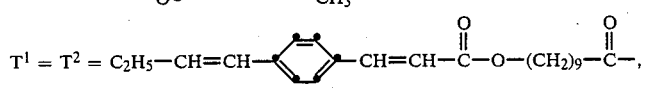
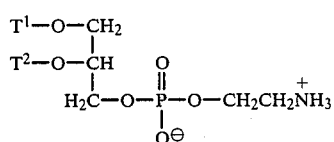
5
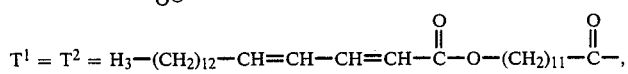
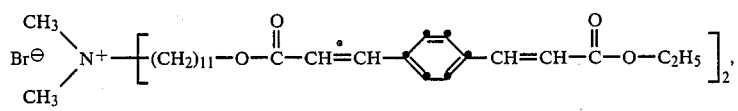
6
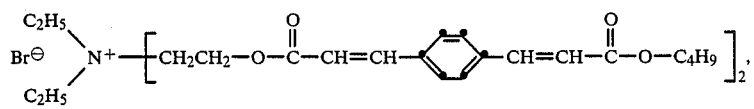
7
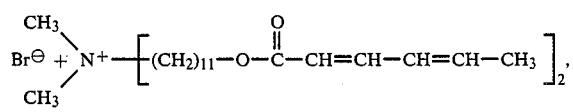
8
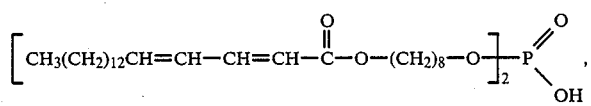
9
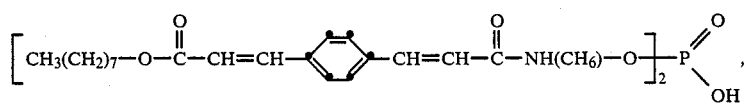
10
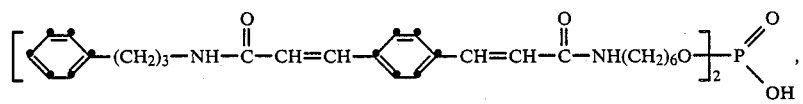
11
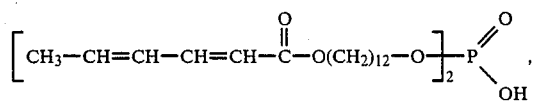
12
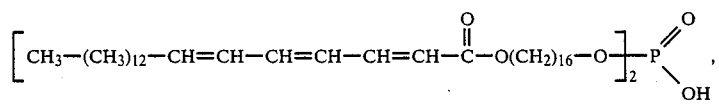
13

-continued
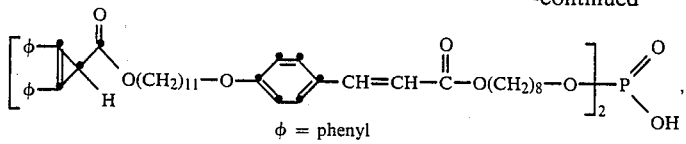
14
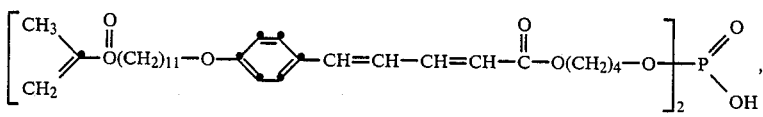
15
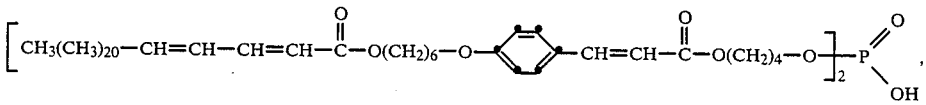
16
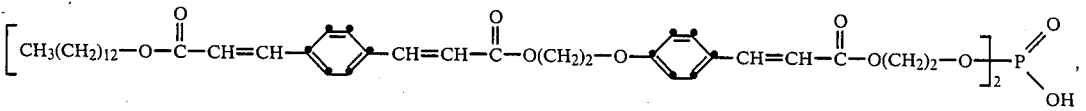
17
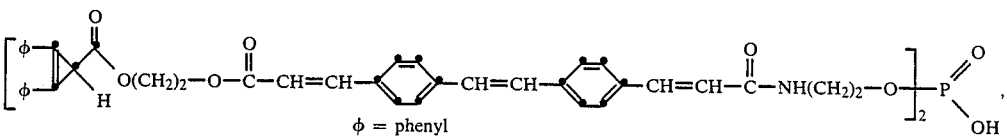
18
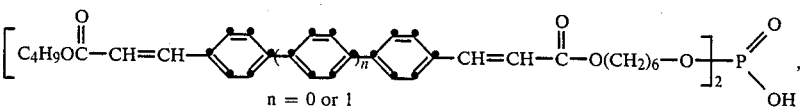
19
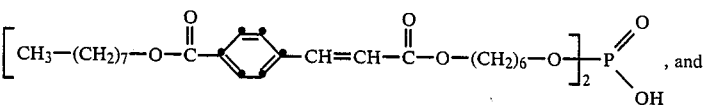, and
20
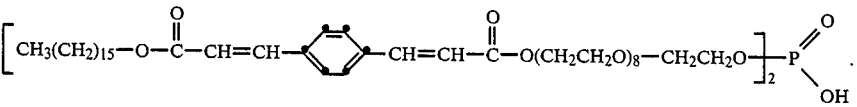
21
* * * * *